United States Patent [19]

Takami

[11] Patent Number: 4,766,126
[45] Date of Patent: Aug. 23, 1988

[54] PROCESS FOR TREATMENT OF NEPHRITIS WITH IMIDAZOQUINAZOLINES

[75] Inventor: Mitsutaka Takami, Tokyo, Japan

[73] Assignee: Daiichi Seiyaku Co., Ltd., Tokyo, Japan

[21] Appl. No.: 800

[22] Filed: Jan. 6, 1987

[30] Foreign Application Priority Data

Jan. 10, 1986 [JP] Japan ................................. 61-3019

[51] Int. Cl.⁴ ................... A61K 31/505; A61K 31/535
[52] U.S. Cl. ..................................... 514/267; 514/254; 514/233.2
[58] Field of Search ............... 544/250; 514/267, 254, 514/239

[56] References Cited

U.S. PATENT DOCUMENTS 4,596,806  6/1986  Ishikawa et al. ..................... 514/267
4,610,987  9/1986  Ishikawa ............................. 514/239

FOREIGN PATENT DOCUMENTS 0129258  12/1984  European Pat. Off. ............ 514/267
0133234  2/1985  European Pat. Off. ............ 514/267

Primary Examiner—Donald G. Daus
Assistant Examiner—Diana G. Rivers
Attorney, Agent, or Firm—Sughrue, Mion, Zinn, Macpeak & Seas

[57] ABSTRACT

An agent for treatment and prevention of nephritis comprising at least one imidazoquinazoline compound represented by formula

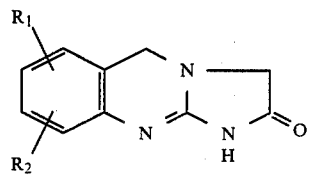

wherein $R_1$ represents a dialkylamino group having 1 to 6 carbon atoms in each alkyl moiety, or an unsubstituted or substituted cyclic amino group; and $R_2$ represents a hydrogen atom, a halogen atom, an alkyl group having 1 to 6 carbon atoms, or an alkoxy group having 1 to 6 carbon atoms, or a salt thereof as an active ingredient.

4 Claims, No Drawings

PROCESS FOR TREATMENT OF NEPHRITIS WITH IMIDAZOQUINAZOLINES

FIELD OF THE INVENTION

This invention relates to an agent for treatment and prevention of nephritis. More specifically, this invention relates to an agent for treatment and prevention of nephritis comprising at least one imidazoquinazoline compound or a salt thereof.

BACKGROUND OF THE INVENTION

Imidazoquinazoline compounds are known to have an inhibitory activity on blood platelet agglutination and an inhibitory activity on metastasis of cancers as described in U.S. Pat. Nos. 4,596,806 and 4,610,987, and Japanese Patent Application (OPI) Nos. 4186/85 and 152416/85 (the term "OPI" as used herein refers to a "published unexamined Japanese patent application").

Clin. Exp. Immunol., Vol. 61, 388–396 (1985) describes a relation between blood platelets and nephritis of acute serum sickness and protection of nephritis by dipyridamole [2,6-bis(diethanolamino)-4,8-dipiperidinopyrimido[5,4,-d]pyrimidine, Merk Index 10th Ed.] as a coronary vasodilator of FUT-175 [2-(6-amino)naphthyl 4-guanidinobenzoate dihydrochloride] as a Clr and Cl esterase inhibitor, but does not refer to effectiveness of imidazoquinazolines according to this invention as an agent for treatment and prevention of nephritis.

SUMMARY OF THE INVENTION

This invention relates to an agent for treatment and prevention of nephritis comprising at least one imidazoquinazoline compound represented by formula (I) hereinafter described or a salt thereof as an active ingredient.

Formula (I) is represented by

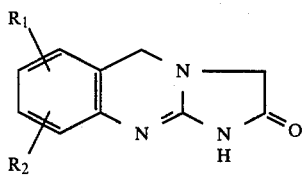

(I)

wherein $R_1$ represents a dialkylamino group having 1 to 6 carbon atoms in each alkyl moiety, or an unsubstituted or substituted cyclic amino group; and $R_2$ represents a hydrogen atom, a halogen atom, an alkyl group having 1 to 6 carbon atoms, or an alkoxy group having 1 to 6 carbon atoms.

As a result of extensive investigations on pharmacological activities of the compounds represented by formula (I), it has now been confirmed that they exhibit an activity to decrease protein in proteinuria accompanying nephritis.

DETAILED DESCRIPTION OF THE INVENTION

The term "cyclic amino group" as used herein for the compounds of formula (I) means a 1-pyrrolidinyl group, a 1-piperidinyl group, a 1-piperazinyl group or a 4-morpholinyl group, and examples of substituents on the cyclic amino group include 1 or 2 alkyl groups having 1 to 6 carbon atoms.

The compounds represented by formula (I) and the pharmaceutically acceptable salts thereof used in the present invention are disclosed in U.S. Pat. Nos. 4,596,806 and 4,610,987, and the most preferred compound for use in the present invention is a 7-piperidino compound and a pharmaceutically acceptable salt thereof as disclosed in U.S. Pat. No. 4,596,806.

The present invention will be described below in detail particularly with reference to 7-piperidino-1,2,3,5-tetrahydroimidazo[2,1-b]quinazolin-2-one dihydrochloride monohydrate (hereinafter referred to as "DN-9693") disclosed in U.S. Pat. No. 4,596,806 as a typical example of the imidazoquinazoline compounds of formula (I), but it is to be noted that other compounds of formula (I) above are also effective as well.

I. Effect on GVHR-Induced Nephritis in Mouse

When an animal of a first filial generation is implanted with lymphatic cells of its parent's line, a graft-versus-host reaction (hereinafter abbreviated as GVHR) takes place to thereby produce an auto-antibody and induce chronic immune-complex (IC) type nephritis.

In this experimentally induced nephritis model, DN-9693 did not influence the production of an auto-antibody but exhibited an effect to decrease protein in urine. This fact suggests that DN-9693 possesses no immune inhibitory activity but anti-phlogistically acts on the inflammatory process to inhibit auto-immune IC type glomerulo-nephritis.

DN-9693 was noted to produce a urinary protein decreasing effect at a low dose level of 1 mg/kg of body weight in the experimental nephritis model and is considered highly promising as a treating agent for nephritis in which an immune-complex takes part.

II. Therapeutic Effect on Lupus Nephritis in Mouse

DN-9693 was administered to $NZB/WF_1$ mice that spontaneously present symptoms resembling general lupus erythematosus in human at a time when the mice showed a high degree of proteinuria. Measurements of protein in urine with time after the administration revealed a reduction of protein in the urine. This result suggests that DN-9693 is also effective on lupus nephritis of spontaneous auto-immune patients.

The present invention will now be illustrated by way of experiment examples. In these examples, the drug of interest was dissolved in a 0.5 wt% aqueous solution of carboxymethyl cellulose and administered to test animals in an amount of 0.1 ml per 10 g of the body weight.

EXPERIMENT EXAMPLE 1

Into $BDF_1$ mice (female; 7-week-old; Nippon Charles River) were intravenously implanted twice spleen cells ($6 \times 10^7$ cells) and thymus cells ($3 \times 10^7$ cells) taken from DBA/2 mice (female; 7-week-old; Nippon Charles River) of their parent's line on the 0 day and the 5th day to thereby induce GVHR. DN-9693 was orally given at a dose level of 1 mg/kg in a single dose per day for consecutive 44 days from the 6th day to the 49th day. After 2 weeks from the first implantation of cells, the protein in urine and the anti-erythrocyte antibody titre were determined at one week intervals. The protein in urine and the antibody titre were determined by the modified one step Exton method and the direct Coombs' test method, respectively, in accordance with the following procedures:

Modified One Step Exton Method

1. Test urine and an albumin standard preparation were placed in a microplate in 10 μl portions.
2. To each hole was added 200 μl of a reagent prepared by dissolving 15 g of sulfosalicylic acid, 20 g of anhydrous sodium sulfate, 5 mg of Bromophenol Blue, and 0.1 g of carboxymethyl cellulose in one liter of water. After stirring to mix, the system was allowed to stand at room temperature.
3. Ten minutes later, the absorbance at 690 nm was measured using the system comprising the reagent alone as a blank.
4. The protein in urine was calculated from a calibration curve.

Direct Coombs' Test Method

1. Blood samples (50 μl) were obtained from the orbital veniplex of the experimental animals (mice) using a heparinized hematocrit tube.
2. The erythrocytes were washed three times by centrifugation (2,500 r.p.m. for 6 minutes) with a phosphoric acid-buffered physiological saline containing 0.3 wt% bovine serum albumin (0.3% BSA-PBS).
3. The erythrocytes were suspended in 0.3% BSA-PBS to prepare a 1 wt% mouse erythrocyte suspension.
4. The erythrocyte suspension (50 μl) was added to 50 μl of rabbit anti-mouse Ig (MBL) in a two-fold serial dilution placed in a microplate. After shaking, the system was allowed to stand at 37° C. for 1 hour and then at room temperature for 2 hours. The state of agglutination was observed.
5. The maximum dilution of the rabbit anti-mouse Ig that gave a positive agglutination was expressed as $10 \times 2^n$, and the value n was taken as an antibody titre.

The results of these tests are shown in Tables 1 and 2. As is shown in Table 1, DN-9693 significantly inhibits an increase of urinary protein at a dose of 1 mg/kg. From Table 2 showing changes of the auto-antibody production, it can be seen that DN-9693 does not decrease the Coombs antibody titre, indicating no influences upon production of an auto-antibody. DN-9693 was thus proved to have a potential activity to lower protein in urine.

TABLE 1

Influence on GVHR-Induced Proteinuria in Mouse

| Group | Number of Animal | Urinary Protein Score (Mean ± S.E.)* | | | |
|---|---|---|---|---|---|
| | | 4th Week** | 5th Week | 6th Week | 7th Week |
| Control | 8 | 0.2 ± 0.1 | 0.8 ± 0.4 | 1.8 ± 0.7 | 2.3 ± 0.6 |
| DN-9693 | 7 | 0.3 ± 0.1 | 0.1 ± 0.1 | 0.4 ± 0.4 | 0.6 ± 0.4*** |

Note:
*0: Urinary protein concentration = not more than 1 mg/ml
0.5: Urinary protein concentration = from 1 to 3 mg/ml
1: Urinary protein concentration = from 3 to 10 mg/ml
2: Urinary protein concentration = from 10 to 30 mg/ml, or not less than 10 mg/ml and ascitic positive
3: Urinary protein concentration = not less than 30 mg/ml, or from 10 to 30 mg/ml and ascitic positive
4: Urinary protein concentration = not less than 30 mg/ml and ascitic positive
**Reckoned from the first implantation of cells.
***Significantly different from the control (P < 0.05)

TABLE 2

Influence on Auto-Antibody Production in Mouse Induced by GVHR

| Group | Number of Animal | Anti-Erythrocyte Antibody Titre (Mean ± S.E.)* | | | | |
|---|---|---|---|---|---|---|
| | | 3rd Week** | 4th Week | 5th Week | 6th Week | 7th Week |
| Control | 8 | 6.3 ± 1.0 | 5.4 ± 0.6 | 4.9 ± 1.3 | 2.9 ± 1.5 | 1.9 ± 1.2 |
| DN-9693 | 7 | 6.6 ± 0.6 | 5.6 ± 0.2 | 3.6 ± 1.1 | 3.9 ± 1.1 | 3.1 ± 1.0 |

Note:
*n: $10 \times 2^n$, n ≥ 1
**Reckoned from the first implantation of cells.

EXPERIMENT EXAMPLE 2

Ten animals clearly showing proteinuria were chosen from 32-week-old NZB/WF$_1$ mice (female, Jackson) and divided into two groups (5 animals per group) taking the protein level in urine as a guide.

DN-9693 was continuously administered orally one or two times per day at a dose of 1 mg/kg, and influences on changes of urinary protein level were examined. The results obtained are shown in Table 3.

In comparing the changes in protein level between the control group and the DN-9693 group taking the level before the administration (32-week-old) as a standard, it can be seen that the increase of urinary protein level is inhibited by the administration of DN-9693. Thus, the activity to lower protein in urine was recognized also in spontaneously occurring lupus nephritis.

TABLE 3

Influences on Urinary Protein in NZB/WF$_1$ Mouse

| Group | Number of Animal | Urinary Protein Index* (Mean ± S.E.) | | |
|---|---|---|---|---|
| | | 0 Week (32)** | 1 Week (33) | 2 Weeks (34) |
| Control | 5 | 1.0 (5)*** | 7.0 ± 5.9 (5) | 4.8 ± 2.9 (4) |
| DN-9693 | 5 | 1.1 (5) | 1.2 ± 0.2 (5) | 1.6 ± 0.6 (5) |

Note:
*Protein level after administration/protein level before administration (32-week-old)
**Period (week) after the commencement of administration. Values in the parentheses are week ages of test animals.
***Values in the parentheses are numbers of survivors.

As is proved by the foregoing experimental results, the imidazoquinazoline compounds of the present invention are effective on various nephritides involving an increase of protein in urine, such as glomerulonephritis, nephrosis, lupus nephritis, and the like.

The agent for treatment and prevention of nephritis according to the present invention is effective through oral administration. It is considered possible to formulate the agent of the present invention into injectable solutions.

The recommended oral dose of the compound of the present invention is from 5 to 50 mg per day for adult human in 1 to 3 divided doses. As the compounds of the invention are rapidly adsorbed when orally administered, and the changes in blood level are close to those when administered intravenously, dose levels similar to those of oral administration are considered applicable to injectable solutions. The $LD_{50}$ of DN-9693 in mice (male, i.v.) was 314.5 mg/kg.

The compounds of the present invention can be formulated into various dosage forms, such as tablets, capsules, powders, liquid preparations, injectable solutions, and the like in a known manner, together with carriers and/or excipients conventionally used in pharmaceutical preparations. A formulation example is described below for illustrative purposes only.

FORMULATION EXAMPLE 1

| | |
|---|---|
| DN-9693 | 30 mg |
| Lactose | 626 mg |
| Corn starch | 300 mg |
| Hydroxypropyl cellulose | 40 mg |
| Magnesium stearate | 4 mg |
| Total: | 1,000 mg |

The above components were mixed, granulated, and compressed into tablets each weighing 100 mg.

While the invention has been described in detail and with reference to specific embodiments thereof, it will be apparent to one skilled in the art that various changes and modifications can be made therein without departing from the spirit and scope thereof.

What is claimed is:

1. A process for treatment and prevention of nephritis which comprises administering to a patient at least one imidazoquinazoline compound represented by the following formula:

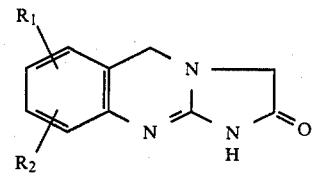

wherein $R_1$ represents a dialkylamino group having 1 to 6 carbon atoms in each alkyl moiety, or a cyclic amino group selected from the group consisting of 1-pyrrolidinyl group, 1-piperidinyl group, 1-piperazinyl group, or morpholinyl group, all of which may be substituted with 1 or 2 alkyl groups having 1 to 6 carbon atoms; and $R_2$ represents a hydrogen atom, a halogen atom, an alkyl group having 1 to 6 carbon atoms, or an alkoxy group having 1 to 6 carbon atoms, or a salt thereof in an amount effective to treat nephritis.

2. A process for treatment and prevention of nephritis as claimed in claim 1, wherein said nephritis is those involving an increase of protein in urine.

3. A process for treatment and prevention of nephritis as claimed in claim 1, wherein said imidazoquinazoline is 7-piperidino-1,2,3,5-tetrahydroimidazo[2,1-b]quinazoline-2-one dihydrochloride.

4. A process for treatment and prevention of nephritis involving an increase of protein in urine as in claim 2 which comprises administering to a patient 7-piperidino-1,2,3,5-tetrahydroimidazo[2,1-b]quinazoline-2-one dihydrochloride.

* * * * *